United States Patent

Hanssen et al.

[11] Patent Number: 6,086,547
[45] Date of Patent: Jul. 11, 2000

[54] WIRE FOR MEDICAL USE COATED WITH POLYETHER SULPHONE AND A COPOLYMER

[75] Inventors: Johannes Hendrikus Leonardus Hanssen, Erlecom; Levinus Hendrik Koole, Gulpen, both of Netherlands

[73] Assignee: Belden Wire and Cable B.V., Venlo, Netherlands

[21] Appl. No.: 09/068,862

[22] PCT Filed: Nov. 27, 1996

[86] PCT No.: PCT/NL96/00467

§ 371 Date: Jul. 23, 1998

§ 102(e) Date: Jul. 23, 1998

[87] PCT Pub. No.: WO97/19712

PCT Pub. Date: Jun. 5, 1997

[30] Foreign Application Priority Data

Nov. 27, 1995 [NL] Netherlands ............................ 1001746

[51] Int. Cl.[7] .................................................. A61M 25/09
[52] U.S. Cl. ............................................ 600/585; 604/280
[58] Field of Search ..................................... 600/585, 433, 600/434, 435; 604/280

[56] References Cited

U.S. PATENT DOCUMENTS

| | | | |
|---|---|---|---|
| 4,534,363 | 8/1985 | Gold | 600/585 |
| 5,001,825 | 3/1991 | Halpern | 600/585 |
| 5,333,620 | 8/1994 | Maitafis et al. | |
| 5,372,144 | 12/1994 | Morher et al. | |
| 5,453,467 | 9/1995 | Bamford et al. | 525/287 |
| 5,749,837 | 5/1998 | Palermo et al. | 600/585 |

FOREIGN PATENT DOCUMENTS

| | | |
|---|---|---|
| 0280732 | 9/1988 | European Pat. Off. |
| 0389632 | 10/1990 | European Pat. Off. |
| 2086400 | 5/1982 | United Kingdom . |
| 95 04839 | 2/1995 | WIPO . |

*Primary Examiner*—Kennedy Schaetzle
*Attorney, Agent, or Firm*—Ladas & Parry

[57] ABSTRACT

The invention relates to a wire for medical use comprising a substrate provided with a first layer and a polymer layer applied thereto, whereby said first layer is polyether sulphone and said polymer layer is a hydrophilic copolymer built up of an N-vinyl lactam compound and an alkyl (meth)acrylate compound. The invention furthermore relates to a method for producing the same and to the copolymer to be used therefor.

34 Claims, 2 Drawing Sheets

WIRE FOR MEDICAL USE COATED WITH POLYETHER SULPHONE AND A COPOLYMER

The present invention relates to a wire for medical use comprising a substrate provided with a first layer and a polymer layer applied thereto. The present invention furthermore relates to a method for producing such a wire.

A wire of this type for medical use is known from European Patent Application 0 389 632. Said European patent application relates to a medical instrument having good sliding properties, such as an instrument used for catheterisation, whereby the surface of a base material, which is coated with a component A, is coated with component B. A polymer having at least one reactive functional group selected from the group consisting of alkali metal alcoholate groups, amino group, alkali metal amide groups, carboxylic acid group, sulphonic acid group, magnesium halogenide groups and fluorinated boron complex groups is used as component A. A hydrophilic polymer having a reactive heterocyclic group being reactive with the reactive functional groups in the component A is used as component B. Several plastics, metallic wires, stainless steel, ceramics and wood are named as the base material. Component A is preferably applied to the base material by dipping or spincoating, using a solution in which a specified amount of component A is dissolved, followed by drying. The proportion of component A in the solution may range from 0.01–50% by weight. Alcohols, halogenated hydrocarbons, ketones, amides and linear or cyclic hydrocarbons are named as solvents. The surface of the base material, which is coated with component A, is then coated with component B dissolved in a solvent, using the same method as used for applying component A. After component B has been applied a reaction is effected between component A and component B by using a heat treatment.

From European Patent Application 0 166 998 a medical instrument is known which comprises a substrate containing a reactive functional group, at least on its surface, which group is covalently bound to a water-soluble polymer or a derivate thereof, as a result of which a lubricating effect is obtained by contacting the treated surface with water. Examples of the reactive functional groups include a diazonium group, azide group, isocyanate group, acid chloride group, acid anhydride group, imino carbonate group, amino group, carboxyl group, epoxy group, hydroxyl group and aldehyde group. The water-soluble polymer is selected from the group consisting of a cellulosic polymer, a maleic acid anhydride polymer, a polyacrylamide and a water-soluble nylon or a derivative thereof.

Further research has shown that a guide wire for medical use, in particular for diagnostic purposes such as catheterisation, must have a very smooth outer surface. During the diagnostic examination the guide wire is introduced into for example the patient's vascular system, and the smooth outer surface of the guide wire ensures that the tissue, in particular the walls of the blood vessels, is not damaged. Since the outer surface is very smooth, the amount of friction is quite low, so that no tissue is damaged. In addition to that the smooth outer surface must comprise a hydrophilic polymer, which makes the guide wire smooth after being immersed in an aqueous solution or a saline solution prior to being introduced into the human body.

The wire according to the invention as referred to in the introduction is characterized in that said first layer is polyether sulphone and that said polymer layer is a hydrophilic copolymer built up of an N-vinyl lactam compound and an alkyl (meth)acrylate compound.

The term "N-vinyl lactam compound" used herein is understood to include N-vinyl pyrrolidone, N-vinyl butyrolactam, N-vinyl caprolactam and the like. Examples of alkyl(meth)acrylate compounds are methyl methacrylate, ethyl methacrylate, propyl methacrylate, n-butyl methacrylate, isobutyl methacrylate, hexyl methacrylate, methyl acrylate, ethyl acrylate, propyl acrylate and hexyl acrylate. The substrate according to the invention is preferably a metal wire.

The hydrophilic copolymer as used on the wire according to the present invention is preferably built up of 1–30% by weight of alkyl (meth)acrylate compound and 99–70% by weight of N-vinyl-lactam compound. If the amount of alkyl (meth)acrylate compound in the hydrophilic copolymer is more than 30% by weight, said hydrophilic copolymer will exhibit insufficient lubricating or sliding action. If the amount of alkyl (meth)acrylate is less than 1% by weight, the hydrophilic copolymer obtained will be insufficiently strong, resulting in an insufficient adherence to the first layer.

The hydrophilic copolymer is preferably built up of N-vinyl pyrrolidone and n-butyl methacrylate, and it is preferred for said monomeric structural units to be randomly distributed over the hydrophilic copolymer. A random copolymer provides an excellent bond between the hydrophilic copolymer and the first layer consisting of polyether sulphone.

The average molecular weight of the hydrophilic copolymer preferably ranges from 50,000–400,000. If the average molecular weight is more than 400,000, the copolymer obtained will be insufficiently flexible and will exhibit a poor bond to the first layer.

The thickness of the polymer layer is preferably 3–8 $\mu$m. If the thickness is less than 3 $\mu$m, the sliding properties obtained will be insufficient, which may lead to the tissue being damaged. If the thickness is more than 8 $\mu$m, a guide wire which cannot be readily spiralled or coiled is obtained.

The present invention furthermore relates to a method for producing the wire. According to this method a metal wire is cleaned in (preferably) a bath of phosphoric acid, then the cleaned wire is passed through a bath of polyether sulphone, the metal wire comprising a layer of polyether sulphone is dried and then passed through a solution in which the hydrophilic copolymer is dissolved, after which the metal wire comprising a polymer layer and a first layer is dried and then wound on a coil.

It is preferred to dissolve the hydrophilic copolymer in N-methyl pyrrolidone in an amount of 10% by weight. It is not possible to dissolve the hydrophilic copolymer in an amount of more than 10% by weight in N-methyl pyrrolidone, this in connection with the solubility of the hydrophilic copolymer in the solvent N-methyl pyrrolidone.

The present invention furthermore relates to a copolymer built up of a N-vinyl lactam compound and an alkyl (meth) acrylate compound obviously intended for coating objects to be used for medical applications. Such objects also include implantation materials which are permanently present in the human body.

The present invention will be explained in more detail with reference to the following example and the appended FIGS. 1 and 2.

The term relative force is understood to mean the force which is required for pulling a guide wire, made from a material according to the present invention, through a polyurethane catheter in comparison with the force which is required for pulling a guide wire provided with a PTFE-layer through the same catheter.

EXAMPLE

The starting materials N-vinyl pyrrolidone and n-butyl methacrylate are charged to a reaction vessel in a mol ratio of 90:10. Then a radical initiator and a chain transfer agent are added, after which the reaction mixture is subjected to a heat treatment in several stages. After said heat treatment in several stages for 14 hours the hydrophilic copolymer is obtained in the form of a white or transparent material. Spectroscopic experiments with an NMR-apparatus have shown that the copolymer is essentially free from monomeric components. The average molecular weight is 78,000, measured according to gel permeation chromatography. Then the copolymer is formed into grains, pulverized and dissolved in an amount of N-methyl pyrrolidone with a proportion of 1:9 (1 part by weight of copolymer:9 parts by weight of solvent).

A stainless steel metallic wire having a diameter of 0.2 mm is cleaned by passing said wire through a bath of phosphoric acid, after which the wire is rinsed in a hot water bath and dried by blowing of hot air. Then the cleaned wire is passed through a 25% by weight solution of polyether sulphone in N-methyl pyrrolidone, as a result of which a polyether sulphone layer having a thickness of about 1 μm is obtained. After evaporation of the solvent at an elevated temperature the coated metal wire is passed through a 10% by weight solution of the aforesaid hydrophilic copolymer in N-methyl pyrrolidone. The wire is passed through the solution 2–3 times, in order to obtain a thickness of about 5 μm, whereby the wire is dried at an elevated temperature each time it has been passed through said solution. Then the metal wire, which is now provided with a first layer and a polymer layer applied thereto, is dried at an elevated temperature and wound on a spool. It is to be understood that a guide wire for medical use is obtained by separating said wire from the spool and making a spring coil from the wire.

Figure 3:
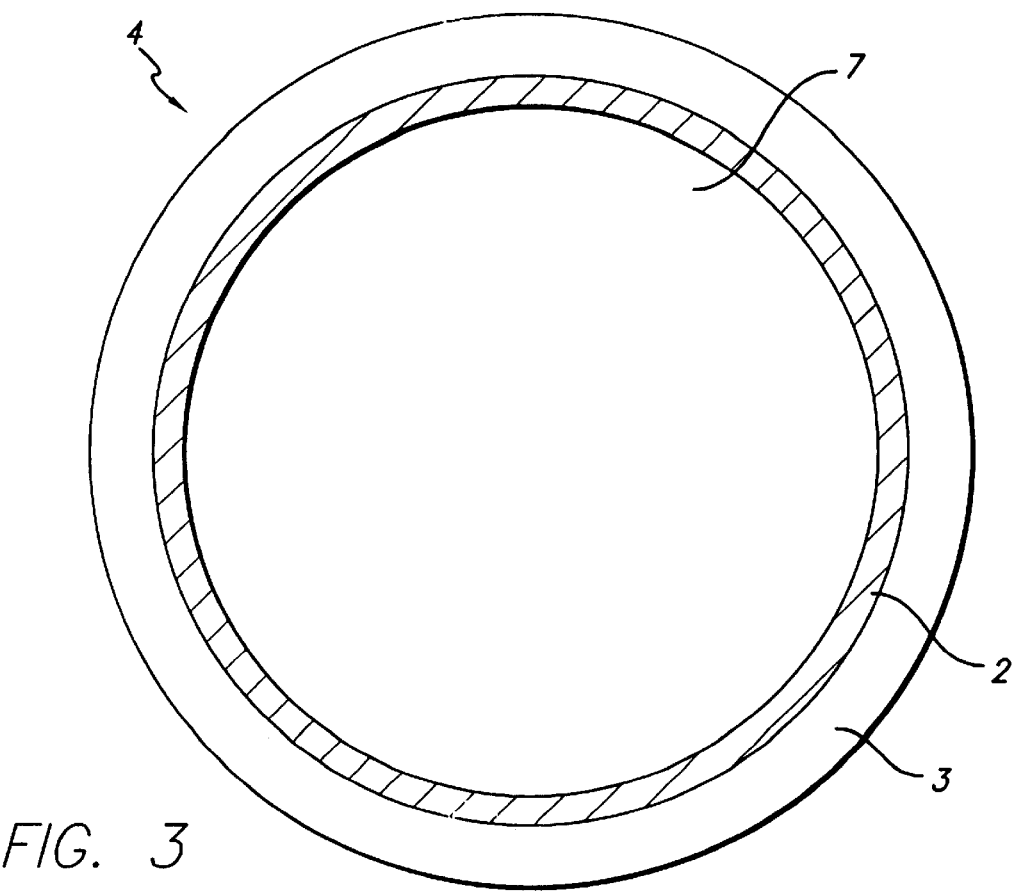
FIG. 3 shows a cross section of a coated wire, comprising a wire coated with a first layer and a second layer.
Figure 4:
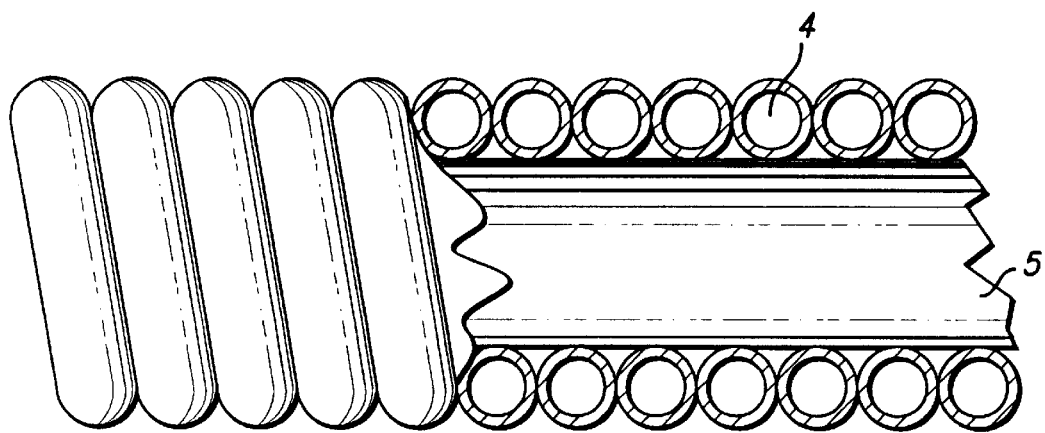
FIG. 4 shows a partial cross section of the coated wire spiralled around a spool.

FIG. 3 shows a cross section of a coated wire 4, comprising a wire 1 coated with a first layer 2 and a second layer 3. FIG. 4 shows a partial cross section of the coated wire 4 spiralled around a spool 5.

Figure 1:
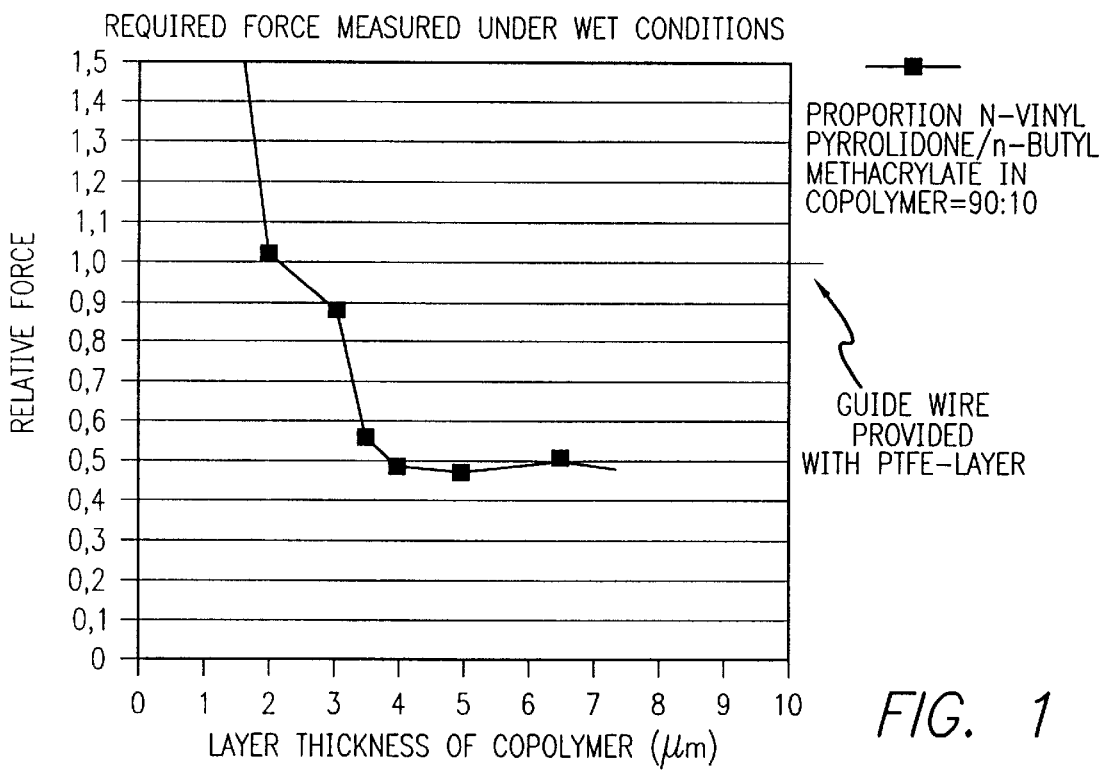
FIG. 1 is a graphic representation of the relative force which is required for pulling a guide wire provided with a hydrophilic copolymer through a polyurethane catheter as a function of the layer thickness of the hydrophilic copolymer.
Figure 2:
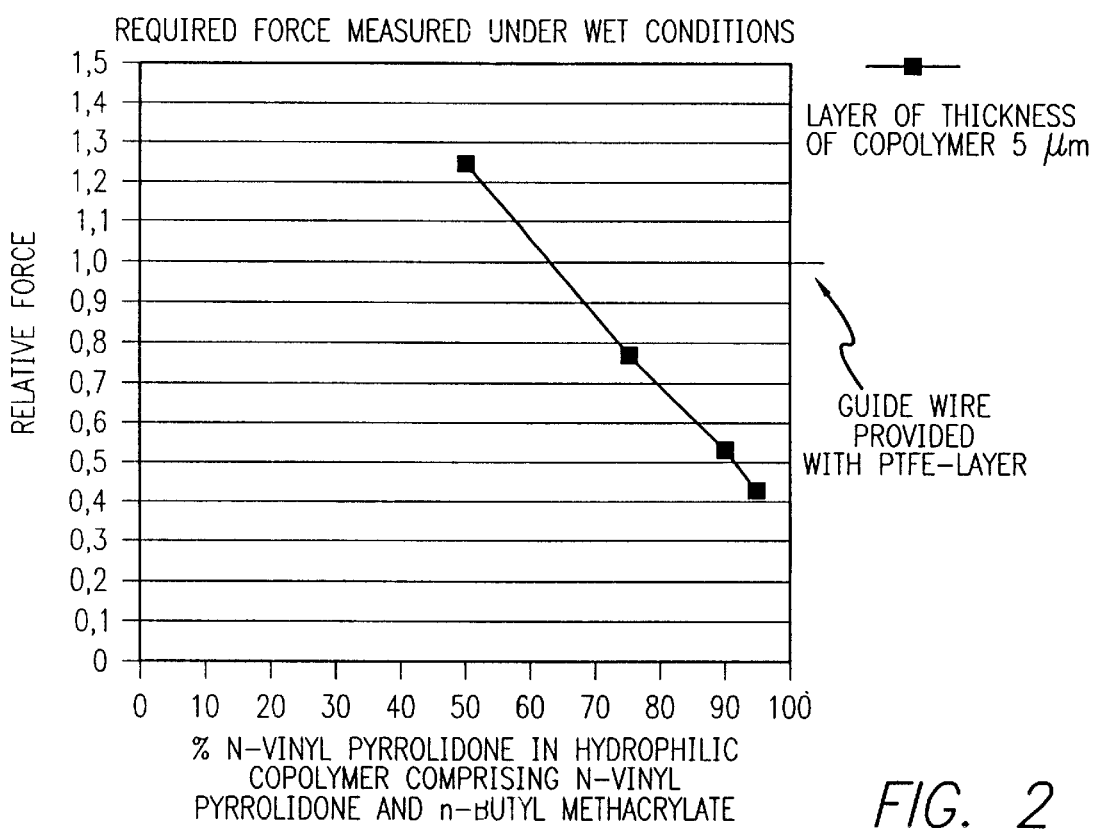
FIG. 2 is a graphic representation of the relative force which is required for pulling a guide wire provided with a hydrophilic copolymer through a polyurethane catheter as a function of the proportion N-vinyl pyrrolidone:n-butyl methacrylate in the hydrophilic copolymer.

A wire provided with layers obtained in this manner was spiralled to form a spring, and subsequently data as shown in the respective FIGS. 1 and 2 were obtained while varying the layer thickness of the hydrophilic copolymer and the percentage of N-vinyl pyrrolidone in the hydrophilic copolymer consisting of the respective monomeric components N-vinyl pyrrolidone and n-butyl methacrylate. FIG. 1 shows the force which is required for pulling such an guide wire coated with a hydrophilic copolymer through a polyurethane catheter as a function of the layer thickness of the hydrophilic copolymer. The molecular proportion of N-vinyl pyrrolidone n-butyl methacrylate in the hydrophilic copolymer is 90:10. This force has been compared with the force which is required for pulling a similar guide wire coated with a PTFE-layer through the same catheter. In FIG. 1 this is shown as a straight line with a relative force having a value 1. FIG. 1 clearly shows that it is preferred for the layer thickness to be more than 3 μm. FIG. 2 corresponds with FIG. 1, wherein FIG. 2 the relative force is shown as a function of the proportion of the monomeric structural units in the copolymer. The layer thickness of the hydrophilic copolymer is 5 μm. From FIG. 2 it is apparent that the percentage of N-vinyl pyrrolidone in the hydrophilic copolymer, consisting of the respective monomeric structural units N-vinyl pyrrolidone and n-butyl methacrylate, is preferably more than 70%, because in such an embodiment the relative force, compared with a guide wire provided with a PTFE-layer, is less than 1.

What is claimed is:

1. A wire for medical use comprising a substrate provided with a first layer and a polymer layer applied to the first layer, wherein said first layer comprises polyether sulphone and said polymer layer comprises a hydrophilic copolymer built up of an N-vinyl lactam compound and an alkyl (meth)acrylate compound.

2. A wire according to claim 1, wherein said hydrophilic copolymer is built up of 1–30% by weight of the alkyl (meth)acrylate compound and 99–70% by weight of the N-vinyl lactam compound.

3. A wire according to claim 1, wherein said hydrophilic copolymer is built up of N-vinyl pyrrolidone and n-butyl methacrylate.

4. A wire according to claim 3, wherein the N-vinyl pyrrolidone and the n-butyl methacrylate are randomly distributed over said hydrophilic copolymer.

5. A wire according to claim 1, wherein an average molecular weight of said hydrophilic copolymer ranges from 50,000–400,000.

6. A wire according to claim 1, wherein said polymer layer has a thickness, and wherein the thickness of said polymer layer is 3–8 μm.

7. A wire according to claim 1, wherein the substrate comprises a metal wire.

8. A method for producing a wire according to claim 1, wherein said wire is cleaned, the cleaned wire is passed through a bath of polyether sulphone, then dried and passed through a solution of said hydrophilic copolymer and, after drying, wound on a spool.

9. The use of a wire according to claim 1 as a guide wire for medical use.

10. A wire according to claim 1, wherein the wire is a guide wire that is spiralled to form a spring.

11. A wire for medical use as claimed in claim 1, wherein said hydrophilic copolymer is built up of 1–30% by weight of N-vinyl pyrrolidone and 99–70% by weight of n-butyl methacrylate.

12. An object for medical use comprising a substrate having a first layer on the substrate and a polymer layer applied to the first layer, wherein said first layer comprises polyether sulphone and said polymer layer comprises a hydrophilic copolymer of an N-vinyl lactam compound and an alkyl (meth)acrylate compound.

13. An object for medical use as claimed in claim 12, wherein said hydrophilic copolymer is built up of 1–30% by weight of the alkyl (meth)acrylate compound and 99–70% by weight of the N-vinyl lactam compound.

14. An object for medical use as claimed in claim 12, wherein said hydrophilic copolymer is built up of N-vinyl pyrrolidone and n-butyl methacrylate.

15. An object for medical use as claimed in claim 14, wherein the N-vinyl pyrrolidone and the n-butyl methacrylate are randomly distributed over said hydrophilic copolymer.

16. An object for medical use as claimed in claim 12, wherein an average molecular weight of said hydrophilic copolymer ranges from 50,000–400,000.

17. An object for medical use as claimed in claim 12, wherein said polymer layer has a thickness, and wherein the thickness of said polymer layer is 3–8 µm.

18. An object for medical use as claimed in claim 12, wherein the substrate comprises a material for implantation into a human body.

19. An object for medical use as claimed in claim 12, wherein the substrate comprises a wire.

20. A method for producing an object for medical use as claimed in claim 12, wherein the method comprises:

passing the object through a bath comprising polyether sulphone;

then drying the object and passing the object through a solution comprising the hydrophilic copolymer of the N-vinyl lactam compound and the alkyl (meth)acrylate compound.

21. A method as claimed in claim 20, wherein the substrate comprises a wire.

22. A method as claimed in claim 21, wherein the wire is a guide wire that is spiralled to form a spring.

23. A method as claimed in claim 20, wherein said hydrophilic copolymer is built up of 1–30% by weight of the alkyl (meth)acrylate compound and 99–70% by weight of the N-vinyl lactam compound.

24. A method as claimed in claim 20, wherein said hydrophilic copolymer is built up of N-vinyl pyrrolidone and n-butyl methacrylate.

25. A method as claimed in claim 20, wherein the solution further comprises a solvent, and wherein the solvent is a solvent for the hydrophilic copolymer and for the polyether sulphone.

26. A method for producing an object for medical use as claimed in claim 12, wherein the method comprises:

passing the object through a bath, wherein the bath comprises polyether sulphone in a solvent;

then drying the object and passing the object through a solution, wherein the solution comprises the hydrophilic copolymer dissolved in the solvent, and wherein hydrophilic copolymer is a copolymer of the N-vinyl lactam compound and the alkyl (meth)acrylate compound.

27. A method as claimed in claim 26, wherein the solvent comprises N-methyl pyrrolidone.

28. A method as claimed in claim 26, wherein the substrate comprises a wire.

29. A method as claimed in claim 28, wherein the wire is a metal wire.

30. A method as claimed in claim 28, wherein the wire is a guide wire that is spiralled to form a spring.

31. A method as claimed in claim 26, wherein said hydrophilic copolymer is built up of 1–30% by weight of the alkyl (meth)acrylate compound and 99–70% by weight of the N-vinyl lactam compound.

32. A method as claimed in claim 26, wherein said hydrophilic copolymer is built up of N-vinyl pyrrolidone and n-butyl methacrylate.

33. An object for medical use as claimed in claim 12, wherein said hydrophilic copolymer is built up of 1–30% by weight of N-vinyl pyrrolidone and 99–70% by weight of n-butyl methacrylate.

34. An object for medical use as claimed in claim 12, wherein the N-vinyl lactam compound is selected from the group consisting of N-vinyl pyrrolidone, N-vinyl butyrolactam, and N-vinyl caprolactam; and wherein the alkyl (meth)acrylate compound is selected from the group consisting of methyl methacrylate, ethyl methacrylate, propyl methacrylate, n-butyl methacrylate, isobutyl methacrylate, hexyl methacrylate, methyl acrylate, ethyl acrylate, propyl acrylate, and hexyl acrylate.

* * * * *